United States Patent [19]
Giuffre

[11] Patent Number: 5,957,853
[45] Date of Patent: Sep. 28, 1999

[54] SELF LEVELLING BIOLOGICAL PRESSURE TRANSDUCER MEANS WITH INPUT EXCITATION VOLTAGE MATCHING AMPLIFIER

[75] Inventor: Kenneth A. Giuffre, Wyckoff, N.J.

[73] Assignee: Vital Evidence, Inc., Wyckoff, N.J.

[21] Appl. No.: 08/953,390

[22] Filed: Oct. 17, 1997

[51] Int. Cl.$^6$ .................................................. A61B 5/00
[52] U.S. Cl. ......................... 600/486; 600/488; 600/561
[58] Field of Search .................................. 600/485, 486, 600/488, 561

[56] References Cited

U.S. PATENT DOCUMENTS

| | | | |
|---|---|---|---|
| 4,776,343 | 10/1988 | Hubbard et al. | 600/488 |
| 4,779,626 | 10/1988 | Peel et al. | 600/488 |
| 5,103,832 | 4/1992 | Jackson | 600/488 |
| 5,280,789 | 1/1994 | Potts | 600/486 |
| 5,697,375 | 12/1997 | Hickey | 600/486 |

*Primary Examiner*—Robert L. Nasser
*Attorney, Agent, or Firm*—McGlew and Tuttle, P.C.

[57] ABSTRACT

A biological pressure measuring system with a transmission device for transmitting a biological pressure at a biological location to a pressure monitor/transducer for measuring the biological pressure. An atmospheric pressure transmission device transmits an atmospheric pressure at a reference location to a reference pressure device for measuring atmospheric pressure and a vertical fluid pressure of the fluid in the atmospheric transmission device. The reference pressure device generates a reference pressure signal with a reference excitation signal representing a pressure of the fluid from the atmospheric pressure transmission device, a vertical distance between the reference location and the reference pressure transducer device being substantially similar to a vertical distance between the transducer and biological location. A signal connection device combines the biological pressure signal and the reference pressure signal into a combined signal. The signal connection device feeds the combined signal into the pressure monitor and combines the biological and reference pressure signals to cause an atmospheric component and a vertical fluid pressure component of the biological and reference pressure signals to substantially cancel each other in the combined signal.

11 Claims, 2 Drawing Sheets

SELF LEVELLING BIOLOGICAL PRESSURE TRANSDUCER MEANS WITH INPUT EXCITATION VOLTAGE MATCHING AMPLIFIER

FIELD OF THE INVENTION

The present invention relates to a system which provides an automatic reference point for transducer setups that convert biological pressure signals from various invasive and noninvasive pressure transmission devices into electrical impulses which can then be converted into usable display modes and(or) stored in various ways.

BACKGROUND OF THE INVENTION

Current biological invasive and noninvasive pressure monitoring systems reference measured pressures to a fixed point of reference, i.e., physical height on the patient's body. The hydrostatic pressure of the atmosphere at that point or reference height then becomes the zero for the system. Pressure impulses in such systems, when conveyed via a fluid conduit to the point of conversion to electrical signal, i.e., the pressure transducer; are usually conveyed to the transducer(s) via a non-compliant flexible tubing means containing a saline solution compatible with blood (e. g. 0.9% in NaCl) and an anticoagulant like heparin sodium which prevents clotting where conveyance fluid interfaces with patient blood, usually in a catheter.

Such transducers when mounted at the patient's bedside, receive via the fluid conduit, an accurate representation of the pressure at the point of measurement (e.g. pulmonary artery, right heart chambers, radial artery, femoral artery, cerebrospinal fluid, et. al.); but only when the monitoring system receiving electrical impulses from the transducers is zeroed to atmospheric pressure at the reference point on the patient's body and only when the transducer(s) are horizontally level with the reference point. When transducer(s) move from this level position, a significant hydrostatic artifact is introduced which corresponds to the positive or negative artifactual pressure exerted on the system by the weight of the effective fluid column of pressure generated within the conveyance conduit as a function of the vertical height difference between proximal and distal ends of the conduit, in this case, the source of pressure on the patient and the transducer.

In order that the pressure transducer(s) do not experience such artifactual error from these vertical height disparities, the transducer(s) are usually mounted in a fixed position that corresponds to the horizontal height of the chosen reference point on the patient (e.g. estimate of right atrial height in cardiovascular measurements, estimate of brain height in neurosurgical patients). This maneuver is known as leveling and it provides for a net zero hydrostatic artifact that might be produced by height differences between patient and transducer(s). Once at level position, the transducer(s) are then zeroed, i.e., exposed to atmospheric pressure by opening the previously closed conduit system to ambient air via a stopcock or other venting device. This zeroing is important because it allows the monitoring system that receives the electrical signal(s) from the transducer(s) to adjust for the inherent zero-offset present in the individual transducers.

Self leveling systems in use utilize a reference probe placed on the patient which is connected via a fluid conduit system either to a differential transducer to provide mechanical subtraction of the resultant hydrostatic height difference between patient reference point and transducer; or to an additional reference transducer mounted at the same height with the pressure measurement transducer(s) which sends electrical signal(s) to a subtraction circuit to provide electrical analog and(or) digital subtraction and hence, correction for any such hydrostatic height differences. Such systems, because they utilize multiple transducers (at least one for height correction and reference), place a significant drain on the amperage required to maintain a constant excitation or input voltage to the transducer setup, and hence to date, can only be used on one specific monitor type whose circuitry has been modified to either adjust to the increased load or to adjust to the reduced resulting output from the transducers in an analog subtraction arrangement.

Biological pressure transduction systems currently utilize multiple methods to transmit pressure signals and convert them into electrical signals which are then delivered to one or several monitoring means and(or) data recording and(or) data storage systems (e.g. U.S. Pat. Nos. 3,946,724, 4,899, 760, 4,890,630, 3,095,872, and 4,779,626) for display and data use.

The method described by J P Blackburn in Br. Med. J.;V.4f825,12/68, provides a means for constant reference between a biological pressure transducer and a patient reference probe. A closed system similar to this is described in U.S. Pat. No. 4,779,626. This system along with that described in U.S. Pat. No. 4,576,035 utilize opposing double-input differential pressure transducers for this purpose. Most recently, U.S. Pat. No. 5,103,832 provides for the use of a single-input non differential pressure transducer by providing a reference probe and subtraction circuitry. Though the systems described provide for more constant external reference to correct for hydrostatic height differences, even those with a separate reference transducer require that the transducer be mounted at an identical height as a single or multiple biological pressure transducers. In any of these systems that use multiple transducers for a single monitoring channel, the circuit characteristics of the monitoring device that supplies input excitation voltage to each monitoring channel must be altered to handle the increased load of additional transducer components without changing the voltage to pressure slope characteristics which are fixed by industry standards.

SUMMARY AND OBJECTS OF THE INVENTION

It is the object of the invention to allow for constant height reference between the patient and the biological pressure transducer(s) involved in measuring various pressures within the patient. The method utilized comprises either a separate reference probe mounted on a fixed point on the patient and connected via a fluid conduit to the reference transducer where the pressure transducer(s) are mounted or a separate reference transducer mounted on the patient leading to a reference probe mounted at the level of the pressure transducers. The input or excitation voltage signal from the monitoring system to each monitoring channel is sensed and amplified with unit gain to adequately supply current to both the reference transducer and the pressure transducer without a change in the excitation voltage; as such a load-induced change in voltage will destroy the stable voltage-to-pressure slope characteristics of the system. This was clearly demonstrated in unsuccessful attempts to prototype the Jackson device (U.S. Pat. No. 5,103,832). Unlike the device, where a reference transducer is directly powered by loading the monitoring system and the signal fed to a subtraction circuit, the system described herein utilizes a unit amplifier which reproduces the voltage supplied by the monitor, reverses its polarity, powers the reference transducer without loading the monitor and hence, without changing the stable voltage-to-pressure slope characteristics of said monitor while directly adding the resultant reference signal directly to the pressure transducer output without the use of a subtraction circuit. While both systems described theoretically correct for the hydrostatic effect of the fluid conduits that normally produce erroneous measurements unless pressure transducers are otherwise leveled to precisely the same height as the patient's right atrium or head depending on the type of monitoring required (cardiovascular vs. cerebrospinal fluid pressures); the system described herein places no additional load on the monitoring system and in addition, is directly attachable without adjustment to a variety of monitoring systems with a variety of supplied transducer excitation voltages including those that utilize an alternating polarity.

A flexible but water-sealed membrane at the terminal end of the conduit attached to the reference transducer allows for the contribution to atmospheric pressure so that channel zeroing may occur without having to disconnect the reference transducer from the addition circuit(s).

Depending on the specific electronics utilized, a single reference transducer and excitation input voltage amplifier of unit gain may be used in parallel to correct one or several pressure transducer addition circuits; or multiple reference transducers can be utilized instead.

It is a further object of the invention, to allow for said reference transducer(s) to be of a different type and have different electrical properties than the pressure transducers (e.g. higher impedance to utilize less current, smaller and even microminiature to take up less space, et. al.). Again, the unit amplifier(s) utilized allow coexistence of transducers with different impedance properties to be used in the same correction circuit. It is a further object of the invention to allow for a reference transducer that is different in properties from the single or multiple pressure measurement transducers thereby allowing ease of placement, longer battery life by using a low-load, high impedance transducer; and even allowing for smaller size for configuration involving placement of said reference transducer directly on the patient. This is accomplished by yoking the reference transducer output(s) either directly to the measurement transducer output(s), or by utilizing matching amplifier(s) that can then be added or subtracted from the original signal depending on the configuration of reference transducer and reference probe. Probe tip or reference transducer must be stably mounted on the patient with the counterpart reference transducer or probe tip(s) stably mounted with the measurement transducer(s).

It is a further object of the invention to make setup easier, safer, and simpler, as pressure transducers no longer have to be mounted in a fixed, level position near the patient. Hence, transducer mounts may be placed in the most convenient location regardless of patient position or movement. Time is saved because precise leveling is not required, and mistakes in positioning that could result in grave inaccuracies affecting clinical decisions are avoided. And a single type of system can be interchanged between different monitoring systems located at different patient locations.

The system described provides for reliable and valid measurements of pressure that are not subject to even slight errors that might occur in the leveling procedure even at the hands of experienced personnel yet versatile enough to be used with any monitoring system regardless of the excitation voltage input, or the current load of the transducer(s) attached.

It is a further object of the invention to provide for stable pressure measurements in environments of unstable G-forces as might occur during extreme flight maneuvers, space flight, zero gravity orbital environments or where patient movement itself produces separate G-forces. In such situations, the reference transducer and reference probe shall be exposed to the same variations in ambient gravity that the measurement transducers are exposed to and hence, can continuously correct for such variations in real time.

It is a further object of this invention to provide additional measurement of G-forces experienced by flight personnel in relation to blood pressure to calculate critical points at which bloodflow to the brain may become impaired, and hence, clear thought and consciousness may become compromised. The method utilized to accomplish this object comprises a minimal-load voltage measurement means at the point of connection between reference transducer output(s) and pressure measurement transducer(s).

According to the invention, the reference transducer, or conversely, the reference probe, shall be firmly mounted to a fixed point on the patient. Since the object of the apparatus is to provide correction of hydrostatic height differences between patient and transducers by either having a reference transducer firmly mounted to the pressure transducer(s), or by having reference transducer(s) mounted anywhere on the patient that shall remain at a stable relative height to the real or theoretical chamber being referenced (e.g. right atrium of the heart). For instance, if a patient were going to remain supine yet undergo extensive upper body surgery, a reference transducer could be reliably mounted on a foot, provided that the height of the foot during the period of measurement remain at the same relative height to said theoretical chamber being referenced (heart right atrium, bead as in neurosurgical patients, et. al.).

When said reference transducer(s) mounted on the patient sits at the same horizontal height as the bedside pressure transducer(s) attached via fluid-filled conduits to a single or multiple measurement sites or catheters on the patient, atmospheric pressure transmitted to the flexible distal end of the fluid conduit connected to said reference transducer acts as a zero reference. When the level of the patient rises above the level of the bedside-mounted pressure transducers, the reference transducer attached to the patient registers a negative hydrostatic pressure transmitted to it by the fluid conduit whose flexible distal end is mounted together at the bedside with said mounted pressure transducers. Conversely, when the level of the patient falls below that of the bedside pressure transducers attached to the distal end of the fluid conduit to the reference transducer, said reference transducer attached to the patient registers a positive hydrostatic pressure.

In the situation where a reference probe is used and the reference transducer is firmly mounted at the same hydrostatic height as the pressure measurement transducer(s), the converse would be true, i.e., when patient level falls below transducer level, the reference transducer would register a negative pressure and vice versa.

The present invention provides a new versatile means that allows for use in various monitoring systems by providing constant hydrostatic height reference via a reference transducer and reference probe that features a separately powered amplifier means instead of a simple analog or digital subtraction means. In such a setup, the input or excitation voltage from the monitoring apparatus is sensed and duplicated to all transducers without a loss in voltage from increased current use by an additional single or multiple reference transducer(s) and adaptable to a variety of excitation voltage sources. In such a system, the output of reference and measurement transducer(s) are then run through another amplifier means which provides subtraction not of the original signal but of the signals now processed to be in proportion to the specific monitoring system. The invention allows a single self-referencing system to be used with a variety of monitoring systems whose input excitation voltage characteristics vary and even those that use alternating excitation voltage polarity in an effort to provide zero-offset and(or) temperature correction.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
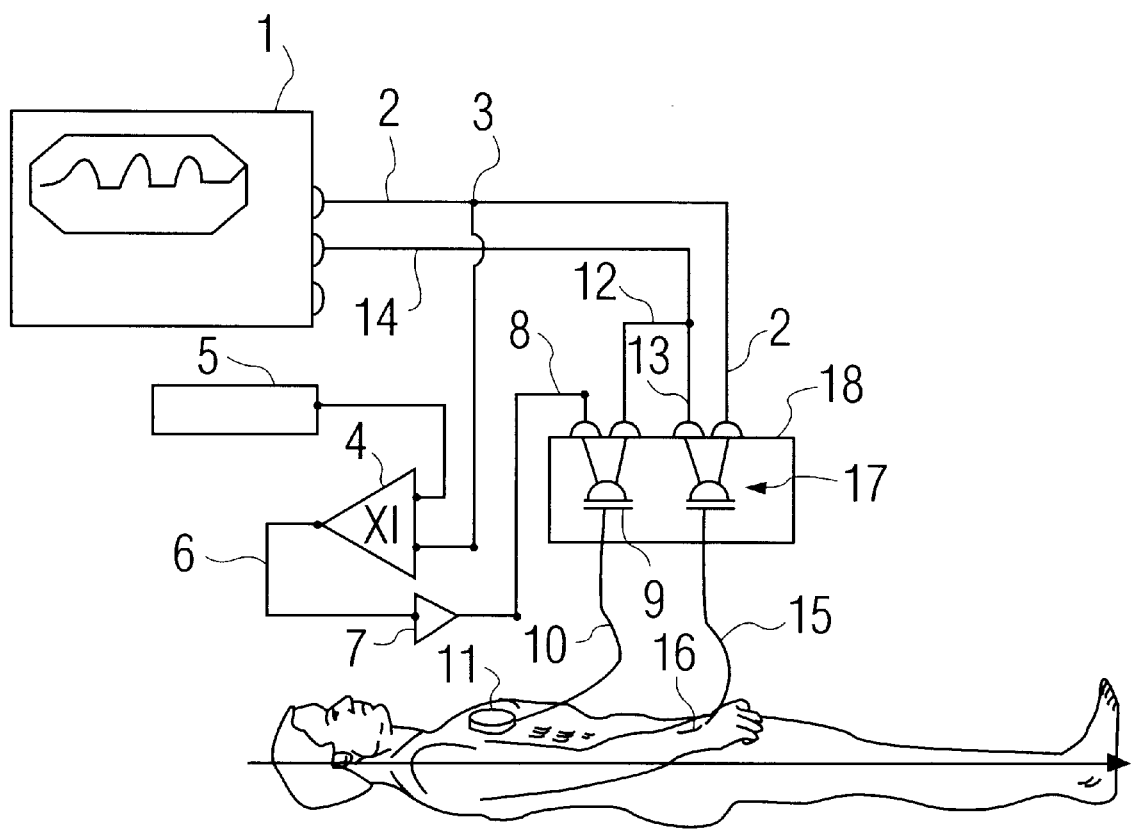
FIG. 1 is a schematic view showing a possible arrangement of 1 monitoring transducer and one reference transducer with the unit amplifier and signal inverter providing excitation voltage to the reference transducer whose output is then combined in parallel with the monitoring transducer. In this figure a single monitoring channel is depicted but it is understood that the reference transducer output can be linked in parallel with 2 or more monitoring output channels for continuous height difference correction.

Referring to the drawings in particular to FIG. 1, the invention embodied therein comprises a biological pressure measurement transducer system, including a biological pressure transmission means originating from biological vessel catheter 16, inserted into the radial artery, and transmitting real-time radial arterial blood pressure to pressure transducer 17 via noncompliant fluid-containing conduit 15. Conduit 15 could be attached to any accessible bodily chamber via a catheter (e.g. Pulmonary artery, internal jugular vein, subclavian vein, femoral artery, etc.). Conduit 15 is filled with a medium such as a fluid with similar density to blood and similar in tonicity (usually 0.9% NaCl in water) with a small amount of the anticoagulant heparin sodium to prevent clotting of the invasive monitoring catheter. A single conduit 15 is used, by a plurality could be used if more than one pressure transducer 17 is used in the case of pressure monitoring at multiple sites.

Monitoring transducers 17 can range in number from one to several and are all connected together in immediate proximity by transducer mounting device 18. Pressure transducer 17 produces analog or digital electrical signals corresponding to the instantaneous pressure level of the medium in the biological pressure transmission means 15 in proportion to the excitation voltage supplied via monitoring system 1 via excitation voltage electrical line 2. Excitation voltage supplied by monitoring system 1 varies slightly from system to system and can even be alternating in polarity to allow for correction of a temperature artifact. The excitation voltage is the same for each channel within a specific monitoring system 1 when more than a single monitoring channel is used by a system for multiple pressure transducers 17.

To correct for a hydrostatic pressure artifact resulting from changes in height between subject and pressure transducer(s) 17 mounted on mounting device 18, a reference transducer 9 provides real-time continuous reference via the following arrangement: Specific monitor system 1 transmits an excitation voltage through electrical line 2 via junction 3 to a high impedance input of unit amplifier 4. Unit amplifier 4 then reproduces the excitation voltage at electrical line 6 while producing negligible current drain from monitoring system 1 via excitation voltage electrical line 2 via junction 3. This is important because any significant current drain off of line 2 besides that utilized by pressure transducer 17 will change the voltage/pressure characteristic slope of the transducer 17 and result in erroneous data passed to monitor 1 via electrical lines 13 and 14.

Hence, the excitation voltage supplied to transducer(s) 17 via electrical line(s) 2 remains at a constant stable value and yet is matched via unit amplifier 4 to electrical output line 6. Amplifier 4 is supplied with current from power source 5. This matched excitation voltage in electrical line 6 is then inverted via polarity inverter 7 and supplies excitation voltage to reference transducer 9 via electrical line 8. Reference transducer 9, mounted to transducer mount 18 and hence, at the same relative vertical height to the subject as pressure transducer 17, is connected to atmospheric reference probe 11 via fluid conduit 10 made of the same material as conduit 15 and containing fluid of identical composition and(or) density as contained within conduit 15.

Reference probe 11 comprises a fluid reservoir covered with an impermeable but flexible membrane to transmit atmospheric pressure to the probe 11 and hence transmit atmospheric pressure to reference transducer 9 via conduit 10 with the addition (or subtraction) of artifactual pressure produced by the hydrostatic height difference between the reference probe 11, placed as a stable reference point on the subject, and reference transducer 9. The resulting artifactual pressure is converted via reference transducer 9 into a reference signal of reverse polarity but matched voltage/pressure linearity because its input excitation voltage from electrical line 8 is reversed but matched to input excitation voltage from monitor 1 to electrical input line 2 that supplies the pressure transducer(s) 17 with input excitation voltage. The output from reference transducer 9, which is proportional to the height difference between subject and pressure transducer but reverse in polarity, is then joined in parallel via electrical line 12 to pressure transducer(s) 17 output electrical line(s) 13. The resulting electrical signal(s) transmitted through electrical line(s) 14 produces continuously height-corrected pressure reading(s) in monitor system 1.

Figure 2:
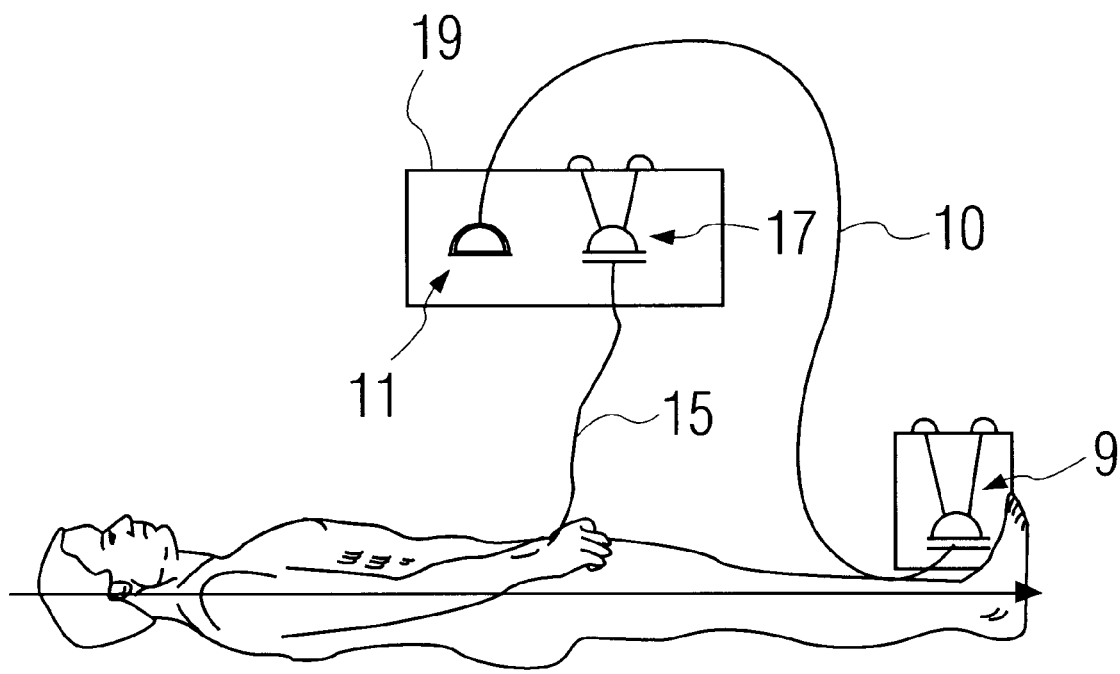
FIG. 2 is a view of an alternate method of mounting a reference transducer and reference probe such that instead of mounting the reference probe to a fixed point on the patient, the reference transducer is mounted at the fixed point, eliminating the need for the signal inverter at the output of the unit amplifier shown in FIG. 1.

In the case where it is more convenient to mount a small reference transducer 9 directly to the patient on a fixed point as shown in FIG. 2, the signal polarity inverter 7 can be eliminated. Here in FIG. 2, rather than reference probe 11 being mounted on a stable point on the subject, it is mounted via mounting means 19 at the same level as the pressure transducer(s) 17 with conduits 10 and 15 serving the same role as in FIG. 1.

While a specific embodiment of the invention has been shown and described in detail to illustrate the application of the principles of the invention, it will be understood that the invention may be embodied otherwise without departing from such principles.

I claim:

1. A transducer system for measuring biological pressure of a patient, the system comprising:

biological pressure transmission means for transmitting a biological pressure of the patient at a biological location via a fluid to a transducer location;

pressure monitor for measuring said biological pressure, said pressure monitor generating a biological excitation signal, said pressure monitor including biological transducer means at a transducer location for receiving said fluid from said biological transmission means and generating a biological pressure signal with said biological excitation signal representing a pressure of said fluid from said biological transmission means at said transducer location;

an atmospheric pressure transmission means for transmitting an atmospheric pressure at a reference location;

reference pressure means for measuring atmospheric pressure and a vertical fluid pressure of said fluid in said atmospheric transmission means, said reference pressure means including amplifier means for generating a reference excitation signal from said biological excitation signal, said reference pressure means including a reference pressure transducer means for receiving said fluid from said atmospheric pressure transmission means and generating a reference pressure signal with said reference excitation signal representing a pressure of said fluid from said atmospheric pressure transmission means, a vertical distance between said reference location and said reference pressure transducer means being substantially similar to a vertical distance between said transducer and biological location;

signal connection means for combining said biological pressure signal and said reference pressure signal into a combined signal, said signal connection means feeding said combined signal into said pressure monitor, said signal connection means combing said biological and reference pressure signals to cause an atmospheric component and a vertical fluid pressure component of said biological and reference pressure signals to substantially cancel each other in said combined signal.

2. A system in accordance with claim 1, wherein:

said amplifier means generates said reference excitation signal without substantially altering said biological excitation signal from said pressure monitor.

3. A system in accordance with claim 1, wherein:

said reference location is at a height substantially equal to said biological location and said reference pressure transducer means is a height substantially equal to said transducer location.

4. A system in accordance with claim 1, wherein:

said reference location is at a height substantially equal to said transducer location and said reference pressure transducer means is a height substantially equal to said biological location.

5. A system in accordance with claim 1, wherein:

said signal connection means connects said reference and biological pressure signals together in parallel.

6. A system in accordance with claim 1, wherein:

said reference pressure transducer means and said biological pressure transducer means have different impedance characteristics except for an excitation signal to pressure response.

7. A system in accordance with claim 1, wherein:

said biological and reference pressure signals include an acceleration component caused by movement of the patient;

said signal connection means combines said biological and reference pressure signals to cause said acceleration component of said biological and reference pressure signals to substantially cancel each other in said combined signal.

8. A system in accordance with claim 1, wherein:

said reference pressure transducer means has an excitation signal to pressure response substantially similar to an excitation signal to pressure response of said biological pressure transducer means, and a density of said fluid in said biological pressure transmission means is substantially equal to a density of said fluid in said atmospheric pressure transmission means.

9. A system in accordance with claim 1, wherein:

a density of said fluid in said biological pressure transmission means is different than a density of said fluid in said atmospheric pressure transmission means;

said reference pressure transducer means has an excitation signal to pressure response different than an excitation signal to pressure response of said biological pressure transducer means, by an amount to compensate for said difference in said densities.

10. A system in accordance with claim 1, wherein:

said biological excitation signal, said reference excitation signal, said biological pressure signal, said reference pressure signal, and said combined signal are electrical.

11. A system in accordance with claim 1, wherein:

said reference excitation signal is substantially equal in magnitude to, and opposite in polarity from, said biological excitation signal.

* * * * *